US007393692B2

(12) United States Patent
Farquharson et al.

(10) Patent No.: US 7,393,692 B2
(45) Date of Patent: *Jul. 1, 2008

(54) SERS METHOD FOR RAPID PHARMACOKINETIC ANALYSIS OF DRUGS IN SALIVA

(75) Inventors: Stuart Farquharson, Meriden, CT (US); Frank E. Inscore, Bristol, CT (US); Alan D. Gift, Lafayette, IN (US); Chetan S. Shende, Vernon, CT (US)

(73) Assignee: Real-Time Analyzers, Inc., Middletown, CT (US)

( * ) Notice: Subject to any disclaimer, the term of this patent is extended or adjusted under 35 U.S.C. 154(b) by 86 days.

This patent is subject to a terminal disclaimer.

(21) Appl. No.: 11/098,844

(22) Filed: Apr. 5, 2005

(65) Prior Publication Data

US 2006/0084182 A1 Apr. 20, 2006

Related U.S. Application Data

(63) Continuation-in-part of application No. 10/967,486, filed on Oct. 18, 2004.

(51) Int. Cl.
*G01N 21/65* (2006.01)
*G01N 30/14* (2006.01)
*G01N 33/15* (2006.01)
*G01N 30/88* (2006.01)

(52) U.S. Cl. .................. 436/171; 422/61; 422/69; 422/70; 422/82.05; 422/82.09; 422/101; 436/86; 436/92; 436/98; 436/104; 436/161; 436/177; 436/178

(58) Field of Classification Search .............. 422/61, 422/69–70, 82.05–82.09, 101; 436/86, 92, 436/98, 104, 161–162, 164–167, 171–172, 436/177–178
See application file for complete search history.

(56) References Cited

U.S. PATENT DOCUMENTS

| 6,151,522 | A | * | 11/2000 | Alfano et al. ............... 600/473 |
| 6,558,956 | B1 | * | 5/2003 | Carron et al. ............... 436/86 |
| 2003/0211488 | A1 | * | 11/2003 | Mirkin et al. ............... 435/6 |
| 2004/0033613 | A1 | * | 2/2004 | Zwick et al. ............... 436/86 |

OTHER PUBLICATIONS

Harman, A. W. et al, Clinical and Experimental Pharmacology and Physiology 1977, 4, 593-596.*
Dawes, C. P. et al, British journal of clinical pharmacology 1978, 5, 217-221.*
Piraino, A. J. et al, Journal of Pharmacological Methods 1980, 3, 1-7.*
De Gier, J. J. et al, British Journal of Clinical Pharmacology 1980, 10, 151-155.*
Vapaatalo, H. et al, International Journal of Clinical Pharmacology Research 1984, 4, 5-8.*
Nahoul, K. et al, Journal of steroid biochemistry 1987, 26, 251-257.*

(Continued)

*Primary Examiner*—Arlen Soderquist
(74) *Attorney, Agent, or Firm*—Ira S. Dorman

(57) ABSTRACT

The method and apparatus rapidly separate drugs and their metabolites from saliva and, in a continuous sequence of steps, rapidly detect, identify and quantify them through surface-enhanced Raman spectroscopy.

45 Claims, 4 Drawing Sheets

OTHER PUBLICATIONS

Drebing, C. J. et al, Biomedical Chromatography 1989, 3, 217-220.*
Katagiri, Y. et al, Byoin Yakugaku 1989, 15, 437-444.*
Eeg-Olofsson, O. et al, Journal of child neurology 1990, 5, 159-165.*
Sheng, R. et al, Analytical Chemistry 1991, 63, 437-442.*
Petty, C. et al, Spectrochimica Acta 1993, 49A, 645-655.*
Jones, A. W., Clinical Chemistry 1993, 39, 1837-1844.*
Cabalin, L. M. et al, Talanta 1993, 40, 1741-1747.*
Sharonov, S. et al, Analytica Chimica Acta 1994, 290, 40-47.*
Ruperez, A. et al, Applied Spectroscopy 1994, 48, 219-223.*
Sharonov, S. et al, Journal of Raman Spectroscopy 1994, 25, 699-707.*
Jenkins, A. J. et al, Journal of Analytical Toxicology 1995, 19, 359-374.*
Sagawa, K. et al, Pharmaceutical Sciences 1995, 1, 459-462.*
Cardot, J.-M. et al, Biopharmaceutics & Drug Disposition 1995, 16, 603-614.*
Cabalin, L. M. et al, Analytica Chimica Acta 1996, 318, 203-210.*
Rodopoulos, N. et al, Scandinavian Journal of Clinical and Laboratory Investigation 1996, 56, 259-268.*
Sidhu, J. S. et al, American Journal of Tropical Medicine and Hygiene 1997, 56, 13-16.*
Szabo, N. J. et al, Applied Spectroscopy 1997, 51, 965-975.*
Zhang, J. et al. Guangpuxue Yu Guangpu Fenxi 1998, 18, 315-318.*
Brunner, M. et al, British Journal of Clinical Pharmacology 1998, 46, 425-431.*
Szabo, N. J. et al, Applied Spectroscopy 1998, 52, 500-512.*
Lee, Y.-H. et al, SPIE 1998, 3537, 252-260.*
Schulze, H. G. et al, SPIE 1999, 3608, 157-166.*
Speckl, I. M. et al, Clinical Toxicology 1999, 37, 441-445.*
Shephard, S. E. et al, Archives of Dermatological Research 1999, 291, 491-499.*
Angel, S. M. et al, Journal of Raman Spectroscopy 1999, 30, 795-805.*
Bernert, J T., Jr. et al, Journal of Analytical Toxicology 2000, 24, 333-339.*
Edlund, C. et al, Journal of Antimicrobial Chemotherapy 2000, 46, 741-749.*
Carter, J. C. et al, Applied Spectroscopy 2000, 54), 1876-1881.*
Gronholm, M. et al, Forensic Science International 2001, 121, 37-46.*
Yacoubian, G. S., Jr. et al, Journal of psychoactive drugs 2001, 33, 289-294.*
Culea, M. et al, Chromatographia 2001, 53 Supplement, S387-S389.*
Bird, S. M. et al, Journal of cancer epidemiology and prevention 2002, 7, 37-47.*
Nelson, H. S. et al, Journal of Clinical Pharmacology 2002, 42, 319-326.*
Wang, Y. et al, Guangpuxue Yu Guangpu Fenxi 2002, 22, 745-747.*
Samyn, N. et al, Journal of Forensic Sciences 2002, 47, 1380-1387.*
Houlne, M. P. et al, Analytical Chemistry 2002, 74, 4311-4319.*
Wright, C. W. et al, SPIE 2003, 5048, 107-118.*
Sagmuller, B. et al, Journal of Molecular Structure 2003, 661-662, 279-290.*
Wang, Y. et al, Spectrochimica Acta, Part A 2003, 59, 589-594.*
Farquharson, S. et al, Applied Spectroscopy 2003, 57, 479-481.*
Gift, A. et al, SPIE 2004, 5261, 135-141.*
Farquharson, S. et al, SPIE 2004, 5272, 1-6.*
Sepaniak, M. J. et al, American Pharmaceutical Review 2004, vol. 7, pp. 90, 92-97, and 37.*
Trachta, G. et al, Journal of Molecular Structure 2004, 693, 175-185.*
Habrdova, V. et al, GTFCh-Symposium: Ausgewaehlte Aspekte der Forensischen Toxikologie, Beitraege zum Symposium der Gesellschaft fuer Toxikologische und Forensische Chemie, 13th, Mosbach, Germany, 2004, 397-404, Editor: Pragst, F. et al, Publisher: Verlag Dr. Dieter Helm, Heppenheim, Germany.*
Trachta, G. et al, Journal of Raman Spectroscopy 2004, 35, 368-383.*

* cited by examiner

SERS METHOD FOR RAPID PHARMACOKINETIC ANALYSIS OF DRUGS IN SALIVA

CROSS-REFERENCE TO RELATED APPLICATION

This application is a continuation-in-part of copending U.S. patent application Ser. No. 10/967,486, filed Oct. 18, 2004.

STATEMENT REGARDING FEDERALLY SPONSORED RESEARCH AND DEVELOPMENT

The United States Government has rights in this invention pursuant to NIH Contract No. 1R43CA94457-01 and NSF Contract No. DMI-0214280

BACKGROUND OF THE INVENTION

Determining safe and effective dosages for chemotherapy drugs has been and remains a significant challenge in the treatment of cancer, particularly because overdose can be fatal (see Ames B N, Gold L S, Willet W C, "The causes and prevention of cancer", *Proceedings of the National Academy of Science,* 90, 7915-7922, 1995; Dollinger M, Rosenbaum E H, Cable G, *Everyone's Guide to Cancer Therapy.* Kansas City, Mo.: Somerville House Books; 1994). Intercalating drugs, which are the most widely used chemotherapy drugs, prevent cell growth through incorporation into DNA and RNA, which causes improper replication of cancerous cells and incomplete biochemical synthesis. The medicinal success of intercalating drugs is based upon the higher rate of cancer cell multiplication, as compared to that of normal cells. Nevertheless, normal cell growth is also adversely affected, and that is especially true of those cells that involve rapid cell turn-over, such as blood cell production in bone marrow. These dangerous side-effects preclude the use of clinical trials to establish statistical bases for dosages, which are therefore usually derived from knowledge obtained from experience gained with limited sets of previously treated patients.

A secondary approach for determining safe and effective dosage is to monitor metabolism of the drug during administration, with concentrations being adjusted accordingly. Such information can be extremely beneficial and important, since the patient's genetic makeup and nutritional habits can strongly influence the pharmacokinetics of a drug (Ames B N, "Micronutrients prevent cancer and delay aging", *Toxicol. Lett.* 102-103; 5-18, 1998). Unfortunately, current practices require the use of 10-20 mL of blood per analysis (Goodman M, Riley M B. "*Chemotherapy: Principles of administration*" in *Cancer Nursing: Principles and Practice,* 4th ed, Eds: Groenwald S L, Frogge M H, Goodman G, Yarbro C H, Jones and Bartlett: Boston, 1997), and the multiple samples that are required for profiling pharmacokinetics may further jeopardize the patient's health; consequently, they are rarely performed (Cone, E T, Jenkins A J. *Handbook of Analytical Therapeutic Drug Monitoring and Toxicology,* Eds. Wong S H Y, Sunshine I, Chapter 18, CRC Press: New York, 1997).

Saliva analysis has long been considered an attractive potential alternative to the approaches referred to above, and recent research has shown that drug metabolism is often equally represented in saliva as it is in blood plasma, typically at microgram/mL concentrations (van Warmerdam L J, van Tellingen O, ten Bokkel Huinink W W, Rodenhuis S, Maes R A, Bijnen J H, "Monitoring carboplatin concentrations in saliva: a replacement for plasma ultrafiltrate measurements?", *Ther Drug Monit,* 17:5, 465-470, 1995; Takahashi T, Fujiwara Y, Sumiyoshi H, Isobe T, Yamaoka N, Yamakido M, "Salivary drug monitoring of irinotecan and its active metabolite in cancer patients", *Cancer Chemother Pharmacol,* 40, 449-52, 1997; de Jonge M J, J V Verwiej, W J Loos, B K Dallaire, A Sparreboom, "Clinical pharmacokinetics of encapsulated oral 9-amino-camptothecin in plasma and saliva", *Clin Pharmacol Ther,* 65, 491-499, 1999; Joulia J M, Pinguet F, Ychou M, Duffour J, Astre C, Bressolle F (1999) Eur J Cancer 35:296). Analysis of saliva provides a highly desirable option, in that it is non-invasive, reduces the risk of HIV infection, is readily obtained and is relatively easy to analyze chemically. The composition of saliva is 99.5% water, and the concentrations of interfering physiological chemicals are typically at least 100 times lower than in blood plasma or urine (Chamberlain, J., *The Analysis of Drugs in Biological Fluids,* 2nd Ed., CRC Press (1995). Current techniques for saliva analysis, however, like that of blood, require the use of samples of 10 to 20 mL in order to enable chemical separation and detection of drugs and their metabolites, and such quantities are difficult to obtain or generate, as a practical matter.

One approach that is effectively used for measuring chemicals, at concentrations similar to those at which chemotherapy drugs are present in biological fluids, employs surface-enhanced Raman spectroscopy (SERS). The SERS method involves the absorption of incident laser photons within nanoscale metal structures, to generate surface plasmons, which then couple with nearby molecules (the analyte) to thereby enhance the efficiency of Raman scattering, by six orders of magnitude or more (Jeanmaire D L, Van Duyne R P, "Surface Raman Spectroelec-trochemistry", *J. Electroanal. Chem.,* 84, 1-20 (1977); Weaver M J, Farquharson S, Tadayyoni M A, "Surface-enhancement factors for Raman scattering at silver electrodes: Role of adsorbate-surface interactions and electrode structure", *J. Chem. Phys.,* 82, 4867-4874 (1985)). In addition to sensitivity, the rich molecular vibrational information provided by Raman scattering yields exceptional selectivity and allows virtually any chemical to be identified while also distinguishing multiple chemicals in mixtures (see Garrel R L, "Surface-Enhanced Raman Spectroscopy," *Analytical Chemistry,* 61, 401A-411A (1989); Storey J M E, Barber T E, Shelton R D, Wachter E A, Can-on K T, Jiang Y "Applications of Surface-Enhanced Raman Scattering (SERS) to Chemical Detection", *Spectroscopy,* 10(3), 20-25 (1995)).

Four methods have become common in the practice of generating surface-enhanced Raman scattering: (1) the use of activated electrodes in electrolytic cells (see for example Jeanmaire or Weaver above); (2) the use of activated silver and gold colloid reagents (Kerker, M., O. Siiman, L. A. Bumm, D. S. Wang, "Surface-enhanced Raman Scattering of citrate ion adsorbed on colloidal silver," *Applied Optics,* 19, 3253-3255 (1980); Angel, S. M., E. F. Katz, D. D. Archibold, L. T. Ein, D. E. Honigs, "Near Infrared Surface-enhanced Raman Spectroscopy. Part II: Copper and gold colloids," *Applied Spectroscopy,* 43, 367 (1989)); (3) the use of activated silver and gold substrates (Seki., H., "Surface-enhanced Raman Scattering of pyridine on different silver surfaces," *J. Chemical Physics,* 76, 4412-4418 (1982) or Li, Y.-S., T. Vo-Dinh, D. L. Stokes, Y. Wang, "Surface-Enhanced Raman Analysis of p-Nitroaniline on Vacuum Evaporation and Chemical Deposited Silver-Coated Alumina Substrates", *Applied Spectroscopy,* 46, 1354 (1992)); and (4) the use of sol-gels doped with silver or gold particles (Farquharson et al. U.S. Pat. No. 6,623,977, and corresponding International Application Publication No. WO 01/33189 A2, which are commonly owned herewith and the entire specification of which United States patent is hereby incorporated by reference thereto).

Surface-enhanced Raman scattering measurements have been reported for numerous drugs, including sulfa-drugs (Sutherland W S, Lasema, J J, Angebranndt, M J, Wineford-ner, J D "Surface-Enhanced Raman Analysis of Sulfa Drugs on Colloidal Silver Dispersion," *Analytical Chemistry*, 62, 689-693 (1990)), abused drugs (Perez R, Ruperez A, Laserna J J, "Evaluation of silver substrates for surface-enhanced Raman detection of drugs banned in sports practices," *Analytical Chemica Acta*, 376, 255-263, 1998; Carter J C, Brewer W E, Angel S M "Raman spectroscopy for the in situ identification of cocaine and selected adulterants," *Applied Spectroscopy*, 54, 18761881 (2000), and chemotherapy drugs (Rivas L, Murza A, Sanchez-Cortes S, Garcia-Ramos J V, "Adsorption of acridine drugs on silver: surface-enhanced resonance Raman evidence of the existence of different adsorption sites," *Vibrational Spectroscopy*, 25, 19-28, 2001); Nabiev I R, Morjani H, Manfait M, "Selective analysis of antitumor drug interaction with living cells as probed by surface-enhanced Raman spectroscopy," *European Biophysics Journal*, 19, 311-316 (1991); Fabriciova G, Sanchez-Cortez S, Garcia-Ramos J V, Miskovsky P, "Joint application of micro-Raman and surface-enhanced Raman spectroscopy to the interaction study of the antitumoral anthraquinone drugs danthron and quinzarin with albumins," *J Raman Spectrosc* 35 384-389(2004)).

In most of the measurements made in connection with the foregoing, SERS spectra were obtained to demonstrate the ability to identify small quantities of illegal drugs (sulfa-drugs, banned sports drugs, and cocaine) or to elucidate drug structure and surface interactions in binding (acridine, danthron, etc.). In several studies the ability to analyze drugs in urine or plasma by SERS has been suggested, but not successfully performed (Ruperez A, Lasema J J, "Surface-enhanced Raman spectrometry of triamterene on a silver substrate by the nitric acid etching method," *Talanta*, 44, 213-220 (1997); Farquharson S, Lee Y H "Trace drug analysis by surface-enhanced Raman spectroscopy," *SPIE* 4200: 89-95, (2000); Eliasson C, Lore A, Murty K V G K, Josefso M, Kail M, Abrahamsson J, Abrahamsson K, "Multivariate evaluation of doxorubicin surface-enhanced Raman spectra," *Spectrochimica Acta Part A* 57: 1907-1915 (2001)). In the work of Farquharson and Lee, the SERS spectrum of a urine sample from a chemotherapy patient was reported but, due to the presence of dominating obscuring peaks (e.g., of uric acid and creatinine) in the spectra, no drug was identified or quantified. In any event, no known prior art describes or suggests the use of saliva to detect drugs and/or their metabolites by surface-enhanced Raman spectroscopy, albeit papers recently published do allude to such methodologies (Gift A, Shende C, Inscore F, Maksymiuk P, and Farquharson S, "Five minute analysis of chemotherapy drugs and metabolites in saliva: Evaluating Dosage," *SPIE* 5261: 135-141 (2004); Farquharson S, Shende C, Inscore F, Maksymiuk P, and Gift A, "Analysis of 5-fluorouracil in saliva using surface-enhanced Raman spectroscopy," *J Raman Spectrosc*, accepted (2004); Farquharson, S, Inscore, F E, Maksymiuk, P, Gift, A, Shende, C, "Medical applications of surface-enhanced Raman spectroscopy," *Analytical Bioanalytical Chemistry*, submitted, September 2004).

SUMMARY OF THE INVENTION

It is therefore the broad object of the present invention to provide a novel method and apparatus by which drugs and their metabolites in saliva can readily be detected, identified, and quantified. As used herein, the word "drugs" means any chemical substance which, when absorbed by a human being or other saliva-producing animal, may modify one or more of its functions. This includes chemical substances that may be used on or administered to humans or other animals as an aid in the diagnosis, treatment, cure, mitigation, or prevention of disease or other abnormal conditions or to improve general well-being; it also includes chemical substances that may be used, intentionally or unintentionally, to cause injury, illness, or death to humans or other animals, such as poisons. As used herein, the term "drug species" includes drugs, drug metabolites, and mixtures of drugs and their metabolites.

It is a more specific object of the invention to provide each a method and apparatus whereby and wherein the detection, identification and quantification are effected by surface-enhanced Raman spectroscopy.

A further object of the invention is to provide such a method and apparatus whereby and wherein the detection, identification and quantification are carried out simply and in a substantially continuous procedure.

It has now been found that certain of the foregoing and related objects of the invention are attained by the provision of a method for the analysis of saliva by surface-enhanced Raman spectroscopy to enable the presence and concentrations therein of at least one drug species to be determined. The method comprises the steps: obtaining a small sample of saliva; treating the sample of saliva to effect mutual separation of the drug species and interfering chemicals to produce an analyte sample containing the drug species; combining the analyte sample with a SERS-active material; subjecting the combined analyte sample and SERS-active material to SERS to generate a SERS spectrum; and analyzing the SERS spectrum to determine the presence and concentration of the at least one drug species in the analyte sample. The analyte sample may contain at least two different drug species, which may be two or more drugs, two or more drug metabolites, or any combination of drugs and drug metabolites.

The volume of the saliva sample employed will generally be smaller than about 0.5 mL, and will usually be 0.2 mL or less. The interfering chemicals separated will normally constitute all chemicals present in the saliva sample that hinder flow of the drug species to the SERS-active surfaces of the SERS-active material, and/or that chemically deactivate the SERS active surfaces, and/or that produce spectra that would substantially prevent the spectrum of the at least one drug species from being observed. The drug species and interfering chemicals may be mutually separated by a chemical treatment, by a physical treatment and/or by a chromatographic method.

Chemical treatment may employ a solvent for at least one of the drug species and the interfering chemicals. The solvent will desirably be of such polarity as to render it capable of extracting the drug species, and suitable solvents include water containing appropriate acids and bases for pH adjustment; organic liquids such as acetone, acetonitrile, benzene, chloroform, carbon tetrachloride, cyclohexane, dichloromethane, diethyl ether, dimethylsulfoxide, ethyl acetate, ethylene glycol, isopropyl ether, methyl ethyl ketone, n-hexane, tetrahydrofuran, and toluene; and mixtures of such solvents.

Physical treatment for effecting mutual separation may involve passage of the sample through a filter. Suitable filters comprise porous substrates such as paper, coated paper, paper fibers, polymer, polymer fibers, mixed paper and polymer fibers, cellulose acetate, glass wool, cotton, diatomite, porous glass, sintered glass, zirconia-stabilized silica, derivatized silica-based matrices, sol-gels, and derivatized sol-gels. They may also comprise a supported membrane covered with separation materials, such as the silica gels, zirconia-stabilized silica, derivatized silica-based matrices, sol-gels, derivatized sol-gels, glass beads, long-chain alkane particles, derivatized long-chain alkane particles, polymers, derivatized polymers, functionalized membranes, alumina, polystyrene, dendrimers, immobilized crown ethers, and ion-exchange resins. Chromatographic methods may employ the same separation materials, and will desirably utilize a liquid carrier solvent for at least one of the drug(s) and metabolite(s).

In embodiments in which the saliva sample includes at least one metabolite of the drug or drugs present, the SERS spectrum may be analyzed to determine the presence and concentration of both species. In such instances the method may include the additional step of effecting mutual separation of the metabolite(s) and the drug(s), and the chemical and physical treatments, and the chromatographic methods, herein described may also be used for that purpose.

In carrying out the method of the invention for determining pharmacokinetics of a drug, saliva samples will be obtained from a subject at each of a multiplicity of time intervals, to enable changes in the concentrations of the drug(s) and/or the metabolite(s) to be determined over a period of time. The pharmacokinetics of the drugs is then determined by analysis of SERS spectra generated following each of the time intervals.

In particularly preferred embodiments, the steps of treating the saliva sample, combining the analyte sample and SERS-active material, and subjecting the combined analyte sample and SERS-active material to SERS are carried out sequentially, and without substantial interruption. Most desirably, the substantially uninterrupted sequence of steps will also include the steps of obtaining the sample, effecting mutual separation of the drug species, and analyzing the SERS spectra.

The surface-enhanced Raman-active material employed in the method of the invention will normally comprise a metal selected from the group consisting of copper, gold, silver, nickel, and alloys and mixtures thereof. The metal will desirably be of particulate form, or in the form of a surface having a morphology functionally equivalent to metal particles. The surface-enhanced Raman-active material may comprise a chemically synthesized porous structure, such as, in particular, a sol-gel synthesized utilizing a silica-based, titania-based, or zirconia-based alkoxide and at least one surface-enhanced Raman-active metal, and the chemical reaction utilized to synthesize the porous structure will effectively comprise polymerization of at least one monomer that allows the inclusion of a surface-enhanced Raman-active metal. The surface-enhanced Raman-active material may also comprise a mixture of a porous material and at least one surface-enhanced Raman-active metal, wherein the porous material will usually be a sol-gel, silica gel, silica stabilized by zirconia, derivatized silica-based matrix, long-chain alkane particles, and derivatized long-chain alkane particles, and will desirably be effective to produce chemical separations or selective chemical extractions.

Other objects of the invention are attained by the provision of apparatus for the analysis of saliva by surface-enhanced Raman spectroscopy, including means for treating a small sample of saliva to effect mutual separation of at least one drug species and the interfering chemicals, to produce an analyte sample, and means for containing the analyte sample combined with a SERS-active material. The means for containing is connected in direct liquid flow communication with the means for treating, and has at least a section that is constructed to enable effective irradiation of the combined analyte sample and SERS-active material, and collection of surface-enhanced Raman scattered radiation generated thereby. In many instances the means for containing will also include a section for combining the analyte sample and at least one SERS-active material, which combining section lies in direct liquid flow communication with the means for treating. The section for combining may either be physically separated from the section by which radiation is enabled, or the two functions may be performed by a single component. The means for treating may additionally be adapted for effecting mutual separation of at least one drug and at least one metabolite thereof, and the means for containing may be prefilled, to contain at least one SERS-active material; it may also desirably be prefilled to contain a least two different SERS-active materials, arranged seriatim.

As will be appreciated, information obtained using the method of the invention can advantageously be employed to determine the extent to which an administered drug is metabolized during use, the extent to which a prospective drug is metabolized during clinical trials, and the extent to which a chemotherapy drug is metabolized during treatment. It can also be used to determine pharmacokinetics of a drug by measuring multiple samples as a function of time, it can be used to determine pharmacokinetics of a drug for a wide variety of people to establish relationships between drug metabolism and phenotypes and genotypes, attendant to treatment or therapy as well as during clinical trials and also while other classes of drugs are being administered. Pharmacokinetic, phenotype and genotype, and multiple drug use data can be employed to establish dosage; the information obtained can be used to determine pharmacokinetics of a chemotherapy drug during treatment, by measuring multiple samples as a function of time, and to regulate dosage; and information obtained can be utilized to identify a drug or drugs in saliva as illicit, prescribed, or over-the-counter, and to determine the extent of metabolism of such a drug and to establish the extent of an overdose.

Ideally, a swab is used to acquire a saliva sample from a patient's mouth, and a two-phase solvent of water and an immiscible organic liquid is used to separate the drug and it's metabolite from other components of saliva (including a chemical such as thiocyanate, if present). A syringe is then employed to draw the drug-containing phase (normally the organic phase, which will normally also contain any drug metabolites) continuously through a filter or other separation means to remove any residual large molecules (i.e., molecules of 10,000 molecular weight, or higher), such as enzymes or other proteins, thereafter through a silica gel to separate the drug from its metabolites, and then into a glass capillary containing a metal-doped sol-gel used to generate SERS activity; finally, a Raman instrument is used to acquire the SERS spectrum, from which the instrument software detects, identifies and quantifies all of the drugs and their metabolites that were present in the saliva sample.

It will be appreciated by those skilled in the art of chemical separations that many sampling devices can be used to both collect and separate the drugs and their metabolites from saliva and from one another. For example, the pH of the aqueous portion of the two-phase solvent could be adjusted to maximize the amount of thiocyanate that is solvated by the aqueous phase, removing it from the drug species-containing phase. Drawing the organic phase through a polytetrafluoroethylene (TEFLON) ultrafilter, designed to capture protein-sized particles, will allow separation and retention of large molecules of saliva that are in the organic phase, and a silica gel, an ion exchange resin, or another appropriate chromatographic material can be used to separate all of the drugs and metabolites present from one another.

It will also be appreciated by those skilled in the art of SERS that many SERS-active materials and devices can be used to obtain the SERS spectra of the separated drugs and metabolites. In addition to using a single segment of metal-doped sol-gel, multiple segments could be employed that sequentially use sol-gels doped with different metals (e.g., silver and gold), or that contain different metal particles, or that alternatively use alkoxides that are hydrophobic or hydrophilic. Furthermore, metal colloid particles could be added to the sol-gel following gelation, prior to or even after flowing the drugs and metabolites through the sol-gel; a different porous medium could be used that also allows immobilizing SERS-active metal particles, and the SERS-active medium could be contained in a small bore capillary or channel in a microchip device.

The SERS-active medium could be a discrete device such, as an electrode that measures the drugs and metabolites as they flow past it. The SERS-active medium could be incorporated into multi-well plates, such that successive aliquots of the solution containing the drugs and metabolites are dispensed into successive wells each of which is, in turn, interrogated by a Raman instrument to detect, identify and quantify the drugs and metabolites present.

It will further be appreciated by those skilled in the art of chemical separations and SERS that other combinations of materials could be used to perform the analyses described. For example, and perhaps less desirably, a thin layer chromatographic plate, coated with a suitable separation material such as silica gel, could be used to separate the drugs and metabolites from one another. Application of a SERS-active material, such as a silver colloid or a gold vapor to the separated analytes on the plate would enable SERS spectra to be recorded along the axis of chemical separation to detect, identify, and quantify the drugs. Additional variants can of course be employed in the practice of the invention, as will be evident to those skilled in the art.

Any suitable Raman spectrometer, operating at any laser excitation wavelength, can also be utilized. In many instances, however, a 488 to 785 nm interferometer-based system, with wavenumber stability, will be preferred, and a suitable Raman instrument is described in the aforementioned Farquharson et al. U.S. Pat. No. 6,623,977.

DETAILED DESCRIPTION OF THE PREFERRED AND ILLUSTRATED EMBODIMENTS

As indicated above, the present invention provides for a novel method and apparatus for rapidly extracting drug(s) and their metabolite(s) from saliva, and for rapidly detecting, identifying and quantifying the drugs and their metabolites, by surface-enhanced Raman spectroscopy.

The silver-doped SER-active sol-gels employed in the filled glass capillaries utilized in the examples that follow were prepared in accordance with the method of Farquharson et al. U.S. Pat. No. 6,623,977, which capillaries were filled in accordance with the techniques described by Farquharson, S., Gift, A., Maksymiuk, P., and Inscore, F., *Applied Spectroscopy*, 351-354, April 2004 ("Rapid dipicolinic acid extraction from *Bacillus* spores detected by surface-enhanced Raman spectroscopy"). In essence, a silver amine complex, consisting of a 5:1 v/v solution of 1 N AgNO and 28% NHOH, is mixed with an alkoxide consisting of a 2:1 v/v solution of methanol and tetramethyl orthosilicate (TMOS) in a 1:8 v/v silver amine:alkoxide ratio. A 0.15 micro L aliquot of the forgoing mixture is then drawn into a 1-mm diameter glass capillary to fill a 15-mm length. After sol-gel formation, the incorporated silver ions are reduced with dilute sodium borohydride, followed by a water wash to remove residual reducing agent.

Figure 1:
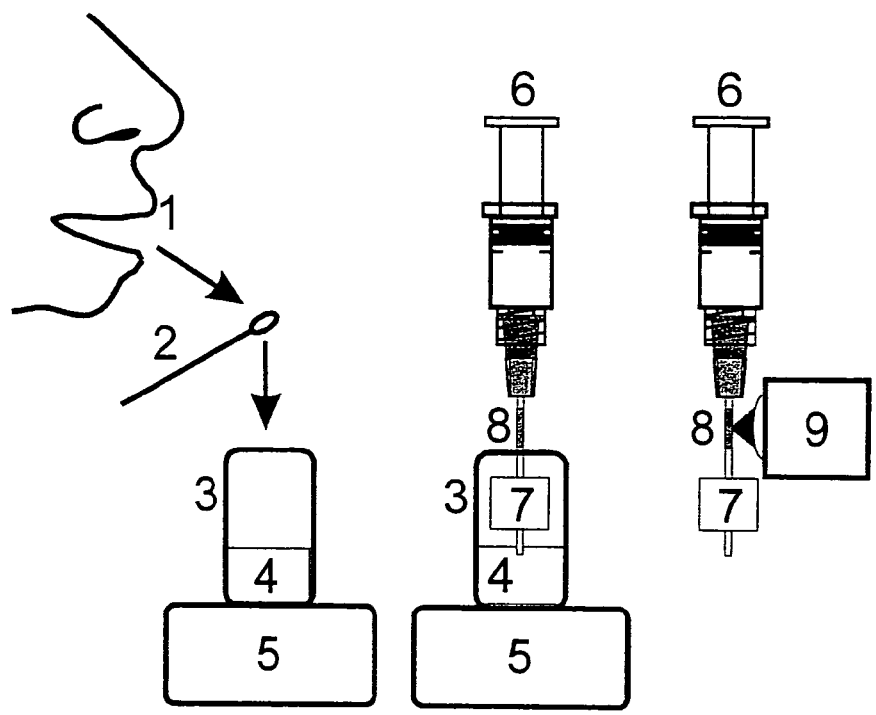
FIG. 1 of the drawings is a schematic diagram showing apparatus embodying the present invention.

FIG. 1 shows the use of a swab, generally designated by the number 2, to collect a saliva sample from a subject's mouth, as required to measure drug(s) and their metabolite(s) of interest, the sample weight being determined by weighing the swab before and after sample collection. The swab 2 is then placed into a container 3, which contains a predetermined volume of a solution 4 that is capable of effectively separating the drug(s) and metabolite(s) from saliva; the container 4 may desirably lie upon a source 5 of heat for increasing the temperature to facilitate the separation (alternatively, a source of a ultrasound may be employed for the same purpose). A syringe 6 is used to draw the sample-containing solution 4 through a filter 7 (serving as a separating means) and into a SERS-active media contained in a capillary section 8, with the syringe/capillary assembly then being located to place the SERS-active media in an appropriate sample holder (not shown) of a Raman instrument (spectrometer) 9, by which the SERS spectrum of the sample is recorded. Computer driven software then analyzes the spectrum to determine if drug(s) and their metabolite(s) are present and, if so, in what quantities.

Figure 3:
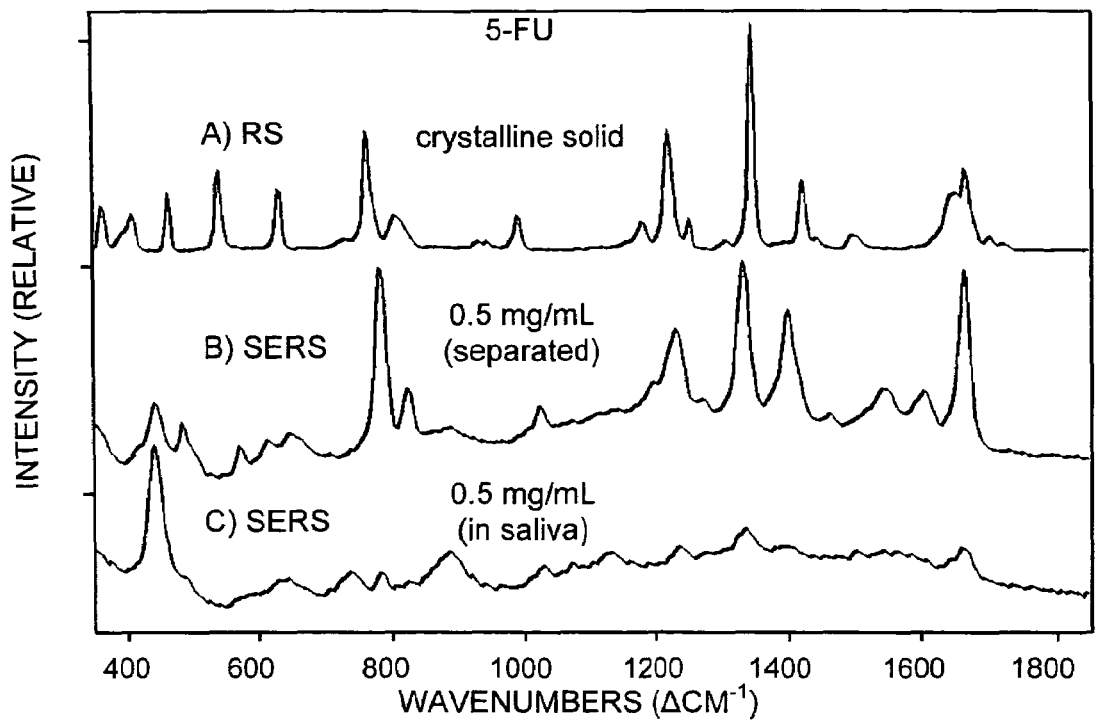
FIG. 3 is a plot of curves (spectra) showing A) the Raman spectrum of a crystalline solid sample of 5-fluorouracil (5-FU) in a glass capillary, acquired in one minute using 150 mW of 785 nm laser excitation; B) the surface-enhanced Raman spectrum of 0.5 mg/mL 5-FU in methanol acquired, in a silver-doped sol-gel filled glass capillary, in one minute using 100 mW of 785 nm laser excitation; and C) the surface-enhanced Raman spectrum of 0.5 mg 5-FU artificially added to 1 mL of saliva, acquired in a silver-doped sol-gel filled glass capillary in one minute using 100 mW of 785 nm laser excitation.

For example, as indicated in FIG. 3, the chemotherapy drug 5-FU produces a unique SER spectrum consisting of major peaks at 786, 1234, 1335, 1400, and 1667 cm$^{-1}$, which can be used to identify its presence. The peak intensities (heights or areas under the peaks) can further be used to quantify the amount of 5-FU (other SERS measurements of 5-FU would normally be used to calibrate the response of the SERS media and Raman instrument).

Figure 2:
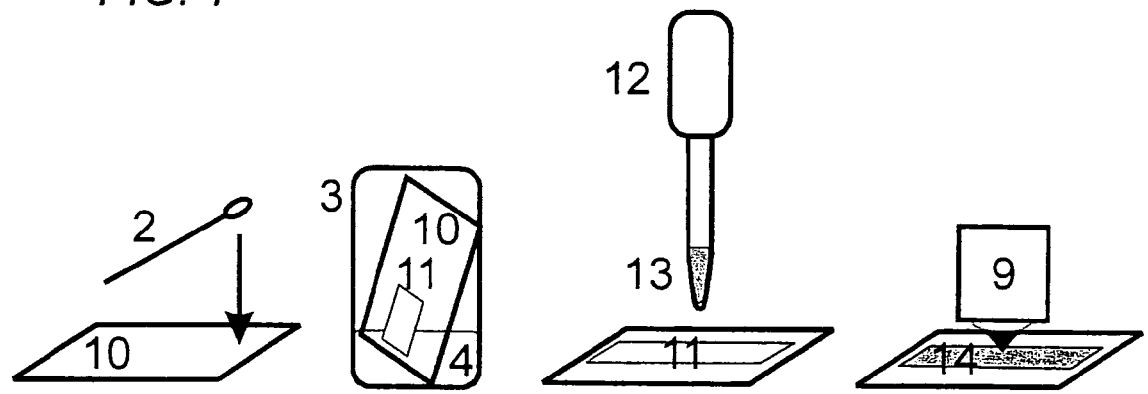
FIG. 2 is a schematic diagram showing an alternative apparatus and procedure embodying the invention.

A second form of apparatus that might be used for carrying out SERS for measuring of drug(s) and their metabolite(s) in saliva is shown schematically in FIG. 2. A thin layer chromatography (TLC) plate, generally designated by the number 10, is employed to separate the drug(s) and their metabolite(s) from saliva. As in the procedure previously described, a swab may be used to collect the sample and deposit it upon the TLC plate. As is generally the practice in TLC, the plate is placed vertically in a container 3 which, in the practice of the present invention, contains a solvent solution 4 that carries the drug(s) and their metabolite(s) up the plate more efficiently by capillary action than it transports less solvated chemical components of the saliva, to produce a band 11 of the analytes on the TLC plate surface.

The plate 10 is then removed from the container 3, and a pipette 12 is used to dispense a drop of a SER-active solution 13, such as a silver colloid, onto the plate 10 over the analyte band 11. Using this arrangement, the Raman instrument 9 is desirably positioned above the sample, and it most suitably scans the TLC band 11 to acquire SERS spectra of the drug(s) and their metabolite(s). Computer driven software again is used to identify and quantify the drug(s) and their metabolite(s), based on peak positions and intensities.

It will of course be appreciated that variations and modifications of the described apparatus and method are wholly within the concepts of the present invention. For example, the apparatus of FIG. 1 could be modified to perform according to the method described in connection with FIG. 2. Specifically, the entire length of sol-gel in the glass capillary shown in FIG. 1 could be completely devoid of metal particles, thus serving, initially, to perform chemical separations only. After introducing the sample, as previously described, a metal colloid solution would be drawn into the capillary, in which case the chemical separation and SERS-generation are carried out as separate steps of the process, as in Example 2. It is also emphasized that other separating materials can of course be used in conjunction with, or in place of, the sol-gel.

The following specific examples are illustrative of the efficacy of the invention, and describe various configurations and applications in which it can be practiced:

EXAMPLE ONE

Analysis of 5-fluorouracil in Saliva

The chemical compound 5-fluourouricil (5-FU) is one of the drugs most often used to treat solid tumors and colorectal carcinoma (Malet-Martino M, Martino R, "Clinical studies of three oral prodrugs of 5-fluorouracil" *The Oncologist*, 1, 288-323 (2002)). In addition to being converted to one of three active forms, 5-FU is converted to an inactive form, dihydrofluorouracil (5-FUH$_2$) by dihydropyrimidine dehydrogenase (DPD). There is a wide genetic-based variation in the amount of DPD in individuals, and the amount of 5-FU converted to 5-FUH$_2$ can range from 15% to 80%. Consequently, employing a "standard" dose of 5-FU has led to severe toxicity, and even death, in individuals deficient in DPD (Diasio R B, Beavers T L, Carpenter J T "Familial deficiency of dihydropyrimidine dehydrogenase" *J Clin Invest*, 81, 47-51 (1988)).

A recent pharmacokinetic investigation has shown that 5-FU concentrations in saliva closely match those in plasma, reaching a maximum of 15-28 microg/mL and a three hour minimum of 0.1 microg/mL (patient dependent, see Joulia above). In the present example, the apparatus and method of the invention are used to measure the concentration of 5-FU in saliva for the purpose of regulating dosage, to thereby minimize toxic effects on a patient-by-patient basis.

Each of three cancer hypothetical patients is given a typical dose of 5-fluorouracil; i.e., 500 mg in 20 cc of a 5% dextrose solution, administered intravenously in 2 minutes. This dosage assumes that the patient has the normal amount of the DPD, which on average metabolizes about 50% of the 5-FU to 5-FUH$_2$. Saliva is collected with a swab from the mouth of each patient minutes after injection, and 0.1 mL is added to a small glass vial containing one mL of a 50/50 aqueous/organic (water and chloroform) solvent. The solution is mildly heated to 50° C., using a heating mantle for one minute, such that any thiocyanate that may be present in the saliva is solvated by the aqueous phase and the 5-FU is solvated by the organic phase. A 1 mL syringe is used to draw the organic portion containing the drug and metabolites, now effectively separated from any interfering thiocyanate, into a 1-mm diameter glass capillary containing two 3-mm segments of sol-gel, the first segment containing undoped sol-gel and the second segment containing sol-gel doped with silver. The first segment acts as a filter for collecting, and removing from solution, large-molecule saliva components, such as proteins and enzymes, whereas the second segment provides a SERS-active medium.

The capillary is mounted in a sample holder of a Raman instrument, which allows focusing 50 to 150 mW of 785 nm laser excitation radiation into the silver-doped sol-gel containing segment of the glass capillary, for collecting the SERS spectrum generated. Computer driven software produces a spectrum of 5-FU similar to that shown in FIG. 3B, the bands observed at 786, 1234, 1335, 1400, and 1667 cm$^{-1}$ being sufficiently unique to ensure that 5-FU is identified as being present. This has been previously verified by measuring both the normal Raman spectra and also the surface-enhanced Raman spectra for this chemical (FIG. 3A). It should be noted that these peaks are not easily discernable in the SERS spectrum of 5-FU in saliva if no chemical separation is performed (FIG. 3C). The intensity of the band at 786 cm$^{-1}$ allows calculation of the 5-FU concentration, the accuracy and precision of the value calculated being based upon measurements performed, prior to the measurement of the oral swab sample, on multiple samples varying in known 5-FU concentrations.

Figure 4:
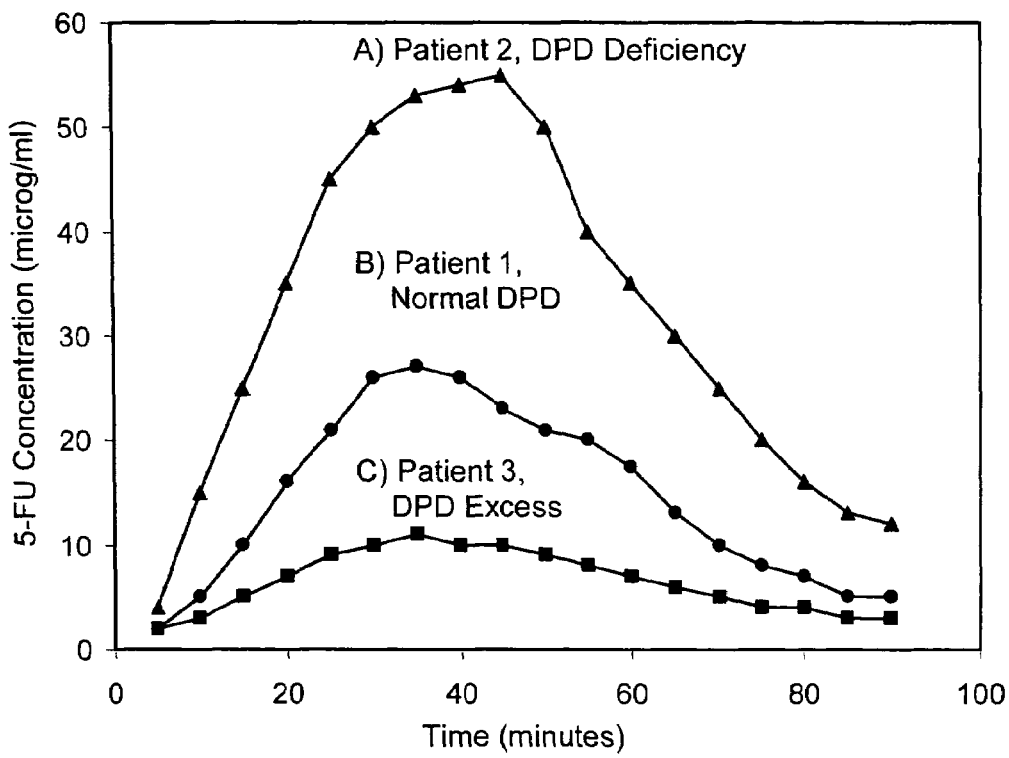
FIG. 4 is a plot of the 5-FU concentration determined, in accordance with the present invention, for multiple saliva samples collected as a function of time for three patients, one patient being deficient in dihydropyrimidine dehydrogenase (DPD), one patent having normal DPD, and one having excess DPD (the measured data points being connected by lines for clarity of presentation)

The result of each measurement made is plotted, as a function of time, to establish that the prescribed dose is safe. In the case of the three hypothetical patients subjected to testing (FIG. 4), Patient 1 is found to have the expected 25 microg/mL 5-FU concentration in his or her saliva, indicating that the standard dosage can be continued, as shown in FIG. 5B.

Patient 2 has a very high concentration of 5-FU in his or her saliva, indicating that a DPD deficiency exists, mandating drastic reduction of the dosage to avoid dangerous side-effects. Patient 3 is found to have a low 5-FU-in-saliva concentration, indicating excess DPD and the need for an increased dosage. It should be noted that this simplified example does not take into account the other reaction rates that form the other active metabolites. It should also be appreciated that measurement of 5-FUH$_2$ along with 5-FU will more accurately determine patient DPD disposition.

EXAMPLE TWO

Analysis of Drug Combinations:

5-fluorouracil and Dacarbazine

Figure 5:
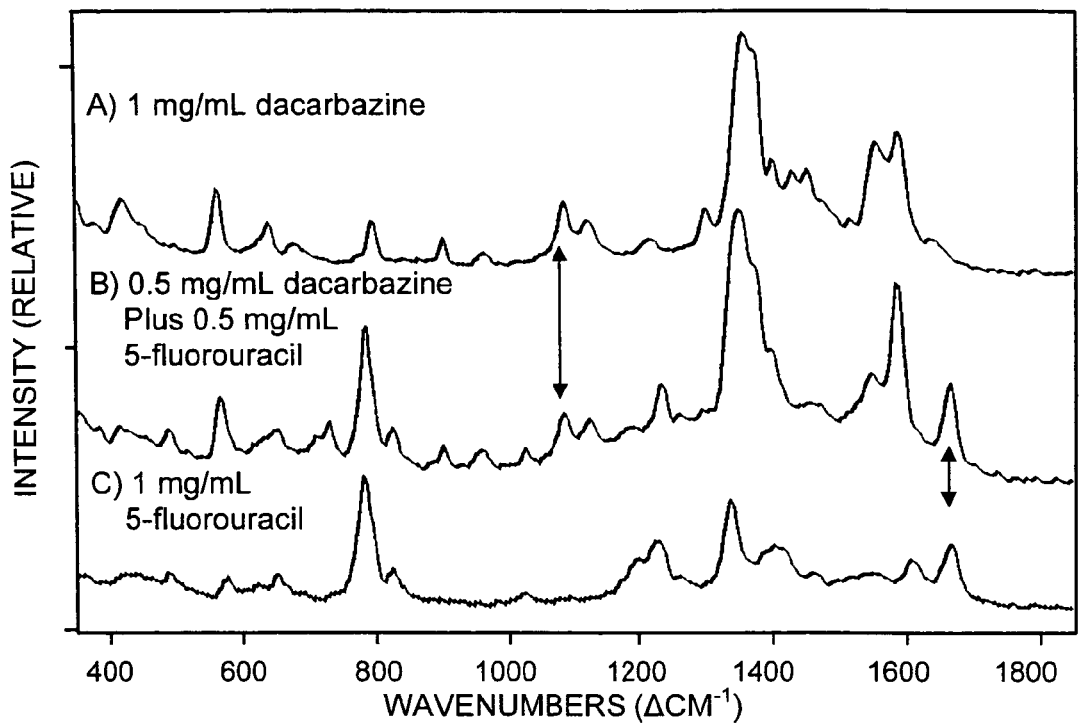
FIG. 5 is a plot of curves showing the SERS spectra of: A) one mg/mL dacarbazine in water; B) a 50/50 mixture of dacarbazine and 5-FU in water, each at 0.5 mg/mL; and C) one mg/mL 5-FU in water, all acquired in silver-doped sol-gel filled glass capillaries in one minute using 100 mW of 785 nm laser excitation, unique peaks for each chemotherapy drug being indicated.

In many cases, two or three chemotherapy drugs are used in combination to improve the chance of killing cancer cells, in which case it will also be desirable to measure each of the drugs. In instances in which each of the drugs contains unique identifying SERS peaks, the exact same procedure as that which is described in Example One can be followed. More particularly, the SERS spectra of dacarbazine, 5-FU, and a 50/50 mixture of the two compounds, in water, are shown in FIG. 5. Although both drugs have peaks near 785 and 1350 cm$^{-1}$, which overlap in the spectrum of the mixture, they also contain unique peaks at 1050 cm$^{-1}$, for dacarbazine, and at 1667 cm$^{-1}$ for 5-FU, which can be used to identify and quantify these drugs in a mixture. The same may not of course be true for other drug combinations, and additional chemical separation may then be required to enable the analysis to be performed at the desired sensitivity.

Figure 6:
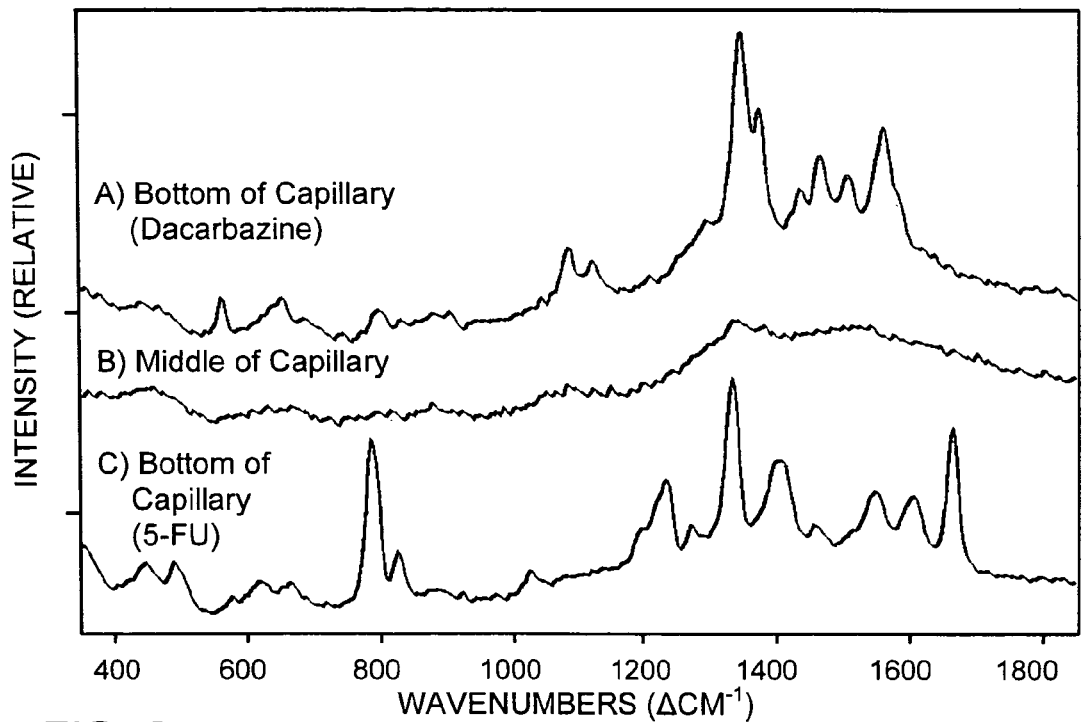
FIG. 6 is a plot of curves showing the SERS spectra acquired in one minute using 100 mW of 785 nm laser excitation, at three positions along a silver-doped sol-gel filled glass capillary, i.e., at: A) the bottom of the capillary, producing a SERS spectrum of dacarbazine; B) at the middle of the capillary, producing an essentially blank spectrum, and C) at the top of the capillary, producing a SERS spectrum of 5-FU and showing ready identification of both drugs.

The latter situation is exemplified by preparing another 50/50 mixture of dacarbazine and 5-FU, and drawing it into a SERS-active capillary. In this case the non-metal doped sol-gel containing segment of the apparatus of FIG. 1 has been replaced by a segment of silica gel. As the sample was drawn through the capillary, the less-polar 5-FU passed through first, ahead of the dacarbazine. After the sample was completely drawn into the silver-doped sol-gel segment, the capillary was mounted in a Raman instrument sample holder, and spectra were recorded at three positions along the capillary, i.e., at the bottom (trailing edge of the sample), middle, and top (leading edge of the sample). As can be seen in FIG. 6, the spectra from the bottom and top positions show nearly pure SERS peaks of dacarbazine and 5-FU, respectively, whereas no definitive peaks were observed in the middle spectrum. Thus, complete separation is obtained, and both drugs can be identified and quantified.

EXAMPLE THREE

Pharmacokinetic Studies of New Drugs:

Parent Drug and Metabolite Measurements

A drug typically requires 12 years to research, develop and bring to market, and generates as much as $500 million per year until generic replacements are introduced (generally coincident with patent expiration). Consequently, every day that introduction of a new drug to market is delayed can represent more than one million dollars in lost revenue.

Clinical trials represent one of the most time-consuming steps entailed in drug development, which trials include measurement of the new drug and its metabolites in blood plasma, to determine pharmacokinetics. The amount of metabolite formed indicates the percent of the parent drug that the body is using, and indicates the dosage size that should be administered. The rate of metabolism indicates how often the drug must be taken. Moreover, in addition to side-effect risks, health factors, such as anemia and possible HIV infection, contribute to limiting the number of willing clinical trial test patients.

Figure 7:
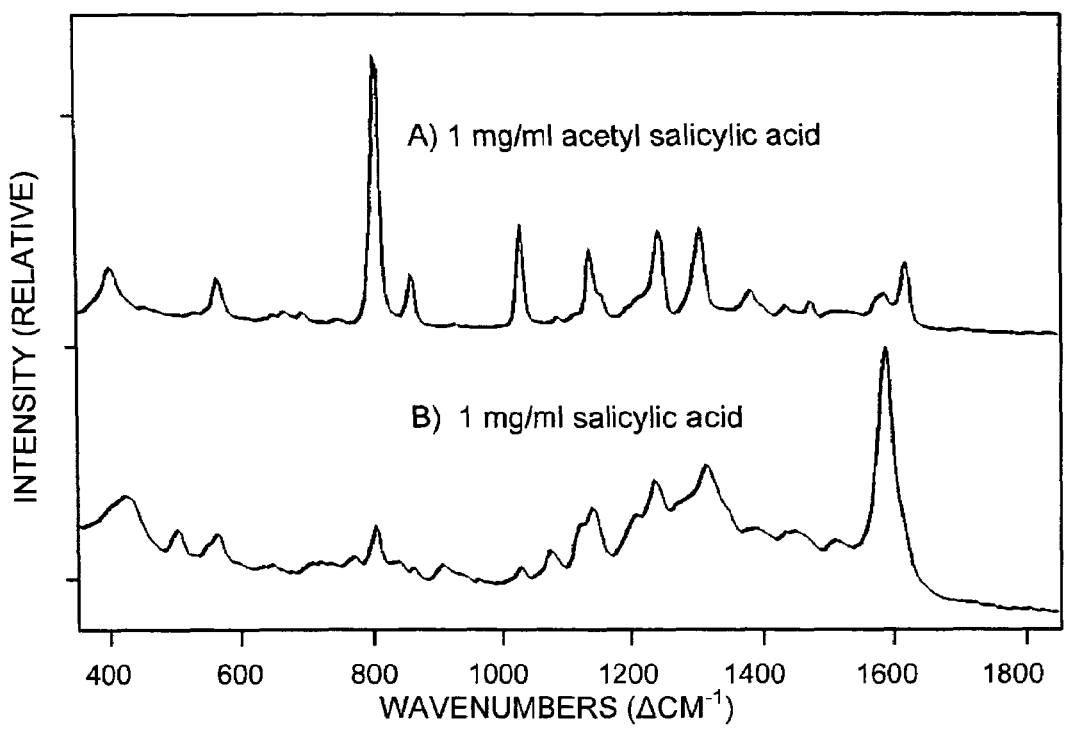
FIG. 7 is a plot of curves showing the SERS spectra of: A) one mg/mL acetylsalicylic acid (aspirin); and B) one mg/mL salicylic acid, its major metabolite, both in water and acquired in silver-doped sol-gel filled glass capillaries in one minute using 100 mW of 785 nm laser excitation.

Again, due to the very small volume of saliva required and its non-invasive and facile sampling, the method and apparatus of the present invention are well suited for use to make repeated, sequential measurements of parent drug and metabolite concentrations in saliva, to determine detailed pharmacokinetics. As in Example One, multiple saliva samples could be collected as often as every five minutes, and analyzed. Rather than using the metal-doped sol-gel capillaries to separate and generate SERS, the saliva sample could, if desired, be swabbed onto the end of a TLC plate, which could then be placed end-on into a container of organic solvent. The combination of capillary action and solvent evaporation carries the parent drug and its metabolite upwardly along the TLC plate, creating a band of separated chemicals. Once sufficient separation has occurred, a pipette could be used to dispense a silver colloid onto the TLC plate, to render it SERS-active for scanning by a Raman probe, as previously described. FIG. 7 shows the SERS spectra of acetylsalicylic acid (aspirin) and one of its major metabolites, salicylic acid. These measurements of drug pharmacokinetics are also used to provide information regarding patient response based on phenotype and genotype.

EXAMPLE FOUR

Detecting Drug Overdose

Yet another important application for the present method and apparatus involves the identification of drugs used in overdose, such as illicit drugs like cocaine, prescription drugs like phenobarbital, and over-the-counter drugs like acetaminophen. Drug identity is extremely important in emergency room situations to enable selection of the appropriate care, because it is often difficult to differentiate the symptoms of overdose resulting from the use of particular drugs. While saliva samples can be collected from the mouth, as described, in the case of cocaine analysis, a nasal sample may be preferred.

In any event, and as previously discussed, the swabbed sample is placed in a two phase solvent to favorably extract the analyte drug or a drug-specific metabolite into the organic phase, which phase is then drawn into a SERS-active capillary through a filter segment to remove any residual saliva components. The capillary is mounted as necessary to enable generation and collection of the surface-enhanced Raman spectrum.

Figure 8:
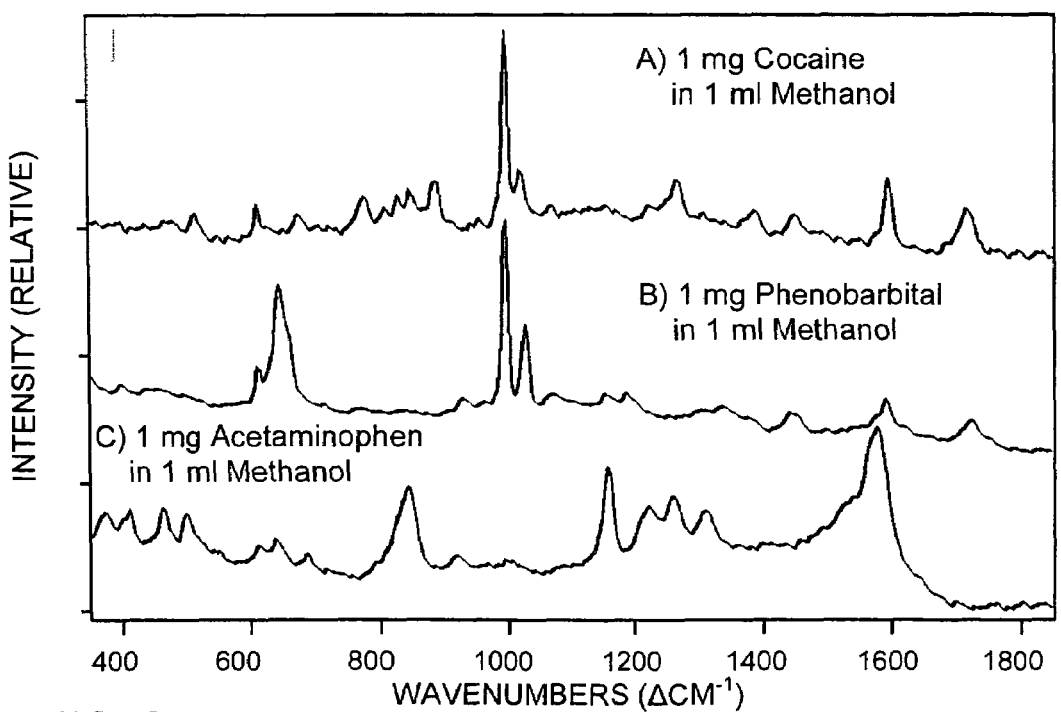
FIG. 8 is a plot of curves showing the SERS spectra of: A) one mg/mL cocaine; B) one mg/mL phenobarbital; and C) one mg/mL acetaminophen, all in methanol and acquired using silver-doped sol-gel filled glass capillaries in one minute using 100 mW of 785 nm laser excitation.

As seen from FIG. 8, cocaine can be identified by the very unique quartet of SERS spectral peaks between 775 and 900 cm$^{-1}$, phenobarbital can be identified by the characteristic broad barbital peak at 650 cm$^{-1}$ in combination with the phenol doublet near 1000 cm$^{-1}$, while acetaminophen can be identified by the broad 825 and 1590 cm$^{-1}$ peaks along with the unique 1175 cm$^{-1}$ peak. In this Example, and for other measurements designed to identify drugs in saliva, full spectral analysis programs are available that can be used to examine and compare all of the peaks in a spectrum so as to ensure successful identification.

Thus, it can be seen that the present invention provides a novel method and apparatus by which drugs and their metabolites in saliva can readily be detected, identified, and quantified. Detection, identification and quantification are effected by surface-enhanced Raman spectroscopy, and the procedure is readily carried out, advantageously in a substantially continuous manner.

Having thus described the invention what is claimed is:

1. A method for the analysis of the saliva of a subject by surface-enhanced Raman spectroscopy to enable determination of the presence and concentration therein of at least one drug species, comprising the steps:
   obtaining a small sample of saliva;
   treating said sample of saliva to effect mutual separation of said drug species and interfering chemicals present in said sample, to produce an analyte sample containing said at least one drug species, said sample treatment including a physical treatment utilizing separation means for removing molecules of 10,000 molecular weight or higher;
   thereafter combining said treated analyte sample with a SERS-active metal-containing material of porous structure and of different character from said separation means;
   subjecting said combined treated analyte sample and SERS-active material to SERS to generate a SERS spectrum;
   analyzing said SERS spectrum to determine the presence and concentration of said at least one drug species in said analyte sample, said steps being repeated sequentially, a multiplicity of times at intervals throughout a time period of 20 minutes or longer, using the saliva of said subject; and
   utilizing information as to the presence and concentration of said at least one drug species in said analyte sample, so determined by said steps so repeated, to in turn determine changes in said concentration of said at least one drug species during said time period and thereby to determine the pharmacokinetics or the extent of metabolism of said at least one drug species.

2. The method of claim 1 wherein said analyte sample contains at least two different drug species.

3. The method of claim 2 wherein said at least two different drug species include at least two different drugs.

4. The method of claim 2 wherein said at least two different drug species include at least two different drug metabolites.

5. The method of claim 1 wherein the volume of each of said obtained saliva samples is less than about 0.5 mL.

6. The method of claim 1 wherein said treatment of said sample for effecting mutual separation of said at least one drug species and said interfering chemicals additionally includes a treatment selected from the group consisting of chemical treatments, chromatographic methods, and combinations thereof.

7. The method of claim 6 wherein said additionally included separation treatment is a chemical treatment effected prior to said physical treatment.

8. The method of claim 7 wherein said chemical treatment employs a solvent for at least one of said at least one drug species and at least certain of said interfering chemicals.

9. The method of claim 8 wherein said solvent is of such polarity as to be capable of extracting said at least one drug species to produce said analyte sample.

10. The method of claim 9 wherein said solvent is selected from the group consisting of water having a selected pH value, acetone, acetonitrile, benzene, chloroform, carbon tetrachloride, cyclohexane, dichloromethane, diethyl ether, dimethylsulfoxide, ethyl acetate, ethylene glycol, isopropyl ether, methyl ethyl ketone, n-hexane, tetrahydrofuran, toluene, and mixtures thereof.

11. The method of claim 1 wherein said separation means comprises a filter, and wherein said physical treatment involves passage of said analyte sample through said filter.

12. The method of claim 11 wherein said filter comprises a porous substrate selected from the group consisting of paper, coated paper, paper fibers, polymer, polymer fibers, mixed paper and polymer fibers, cellulose acetate, glass wool, cotton, diatomite, porous glass, sintered glass, zirconia-stabilized silica, derivatized silica-based matrices, sol-gels, and derivatized sol-gels.

13. The method of claim 11 wherein said filter comprises a supported membrane covered with a separation material selected from the group consisting of silica gels, zirconia-stabilized silica, derivatized silica-based matrices, sol-gels, derivatized sol-gels, glass beads, long-chain alkane particles, derivatized long-chain alkane particles, polymers, derivatized polymers, functionalized membranes, alumina, polystyrene, dendrimers, immobilized crown ethers, and ion-exchange resins.

14. The method of claim 1 wherein said at least one drug species includes at least one drug and at least one metabolite of said at least one drug, and wherein said SERS spectra are analyzed to determine the presence and concentrations of said at least one drug and said at least one metabolite.

15. The method of claim 14 including the additional step of effecting the mutual separation of said at least one drug and said at least one metabolite.

16. The method of claim 15 wherein said additional step of effecting mutual separation of said at least one drug and said at least one metabolite is effected by a treatment selected from the group consisting of chemical treatments, physical treatments, chromatographic methods, and combinations thereof.

17. The method of claim 16 wherein said additional step treatment is a chromatographic method that employs a liquid carrier solvent for at least one of said drug and said metabolite.

18. The method of claim 15 wherein said steps of treating said saliva sample, effecting mutual separation of said at least one drug and said at least one metabolite, combining said analyte sample and SERS-active material, and subjecting said combined analyte sample and SERS-active material to SERS are carried out sequentially and without substantial interruption.

19. The method of claim 14 wherein said method is employed for determining the period of time elapsed since said at least one drug had been administered to a subject.

20. The method of claim 1 wherein said method enables changes in said concentration of said at least one drug to be determined over said time period by analysis of SERS spectra so generated following each of said time intervals.

21. The method of claim 20 wherein said analysis of said SERS spectra, so generated following each of said time intervals, is effected for determining pharmacokinetics of said at least one drug.

22. The method of claim 20 wherein said analysis of said SERS spectra, so generated following each of said time intervals, is effected for determining the extent of metabolism of said at least one drug.

23. The method of claim 1 wherein, for each of said intervals, said steps of treating said saliva sample, combining said analyte sample and SERS-active material, and subjecting said combined analyte sample and SERS-active material to SERS are carried out sequentially and without substantial interruption.

24. The method of claim 23 wherein said substantially uninterrupted sequence of steps includes said steps of obtaining said sample and analyzing said SERS spectrum.

25. The method of claim 1 wherein said SERS-active material comprises a metal selected from the group consisting of copper, gold, silver, nickel, and alloys and mixtures thereof.

26. The method of claim 25 wherein said metal is of particulate form, or is in the form of a surface having a morphology functionally equivalent to metal particles.

27. The method of claim 1 wherein said SERS-active material comprises a chemically synthesized porous structure.

28. The method of claim 27 wherein said SERS-active material comprises a sol-gel, chemically synthesized utilizing a silica-based, titania-based, or zirconia-based alkoxide to produce said porous structure, and at least one surface-enhanced Raman-active metal.

29. The method of claim 28 wherein the chemical reaction utilized to synthesize said porous structure comprises polymerization of at least one monomer that allows the inclusion of a surface-enhanced Raman-active metal.

30. The method of claim 1 wherein said SERS-active material comprises a mixture of a porous material and at least one surface-enhanced Raman-active metal.

31. The method of claim 30 wherein said porous material is effective to produce chemical separations or selective chemical extractions.

32. The method of claim 30 wherein said porous material is selected from the group consisting of sol-gels, silica gels, silica stabilized by zirconia, derivatized silica-based matrices, long-chain alkane particles, and derivatized long-chain alkane particles.

33. The method of claim 1 wherein said saliva samples are collected as often as every five minutes.

34. The method of claim 1 wherein said interfering chemicals constitute all chemicals present in said saliva sample that hinder flow of said at least one drug species to the SERS-active surfaces comprising said SERS-active material, and/or that chemically deactivate said SERS-active surfaces, and/or that produce spectra that would substantially prevent the spectrum of said at least one drug species from being observed.

35. The method of claim 1 wherein said method is employed for setting the initial dosage of said at least one drug to be administered to a subject.

36. The method of claim 1 wherein said method is employed for controlling the dosage of said at least one drug to be administered to a subject.

37. The method of claim 1 wherein the identity of said at least one drug species is unknown, and wherein said analysis of said SERS spectrum is utilized to determine said species identity.

38. The method of claim 37 including a step of matching said SERS spectrum with SERS spectra stored in a library, for making said species identity determination.

39. The method of claim 37 including a step of comparing the concentration of said identified at least one drug species to standard dosages of a drug that constitutes, or that is a metabolite precursor to, said identified species, to determine if an overdose or an underdose has been administered to said subject.

40. The method of claim 37 including the steps of determining the pharmacokinetics of said identified at least one drug species, and comparing said determined pharmacokinetics to known pharmacokinetics for said identified drug species to determine when a drug that constitutes, or that is a metabolite precursor to, said identified drug species was administered to said subject.

41. The method of claim 1 wherein said steps of treating said sample to remove molecules of 10,000 molecular weight or higher, and of combining said analyte sample with a SERS-active material, are effected by drawing said analyte sample through physical treatment separation means and into said SERS-active material.

42. The method of claim 41 wherein each of said physical treatment separation means and said SERS-active material comprises a sol-gel.

43. The method of claim 42 wherein said sol-gel of said physical treatment separation means and said SERS-active sol-gel are disposed directly adjacent to one another, and said analyte sample is transported through said physical treatment separation means sol-gel and thereafter through said SERS-active sol-gel.

44. The method of claim 1 wherein the volume of each of said obtained saliva samples is less than about 0.2 mL.

45. A method for the analysis of the saliva of a subject by surface-enhanced Raman spectroscopy to enable determination of the presence and concentration therein of at least one drug species, comprising the steps, carried out in a period of about five minutes:
    obtaining a less than 0.5 mL sample of saliva;
    treating said sample of saliva to effect mutual separation of said drug species and interfering chemicals present in said sample, to produce an analyte sample containing said at least one drug species, said sample treatment including a physical treatment utilizing separation means for removing molecules of 10,000 molecular weight or higher;
    thereafter combining said treated analyte sample with a SERS-active metal-containing material of porous structure and of different character from said separation means;
    subjecting said combined treated analyte sample and SERS-active material to SERS to generate a SERS spectrum;
    analyzing said SERS spectrum to determine the presence and concentration of said at least one drug species in said analyte sample, said steps being repeated sequentially, a multiplicity of times at intervals throughout a time period of 20 minutes or longer, using the saliva of said subject, and for each of said intervals said steps of treating said saliva sample and combining said analyte sample and SERS-active material being carried out sequentially and without substantial interruption; and
    utilizing information as to the presence and concentration of said at least one drug species in said analyte sample, so determined by said steps so repeated, to in turn determine changes in said concentration of said at least one drug species during said time period and thereby to determine the pharmacokinetics or the extent of metabolism of said at least one drug species.

* * * * *